United States Patent [19]

Kimpara et al.

[11] Patent Number: 4,525,200

[45] Date of Patent: Jun. 25, 1985

[54] AQUEOUS-SOLUBLE COMPOSITIONS FOR ADJUSTING GROWTH OF ORNAMENTAL AND CROP PLANTS

[75] Inventors: Masaomi Kimpara, Shizuoka; Munehiro Suzuki, Toyohashi, both of Japan

[73] Assignee: American Cyanamid Company, Stamford, Conn.

[21] Appl. No.: 468,441

[22] Filed: Feb. 22, 1983

[51] Int. Cl.$^3$ .............................................. A01N 25/30
[52] U.S. Cl. ........................................ 71/76; 71/181; 71/DIG. 5
[58] Field of Search ...................... 71/DIG. 5, 121, 76

[56] References Cited

U.S. PATENT DOCUMENTS

| | | | |
|---|---|---|---|
| 3,156,554 | 11/1964 | Tolbert | 71/121 |
| 3,819,357 | 6/1974 | Epstein et al. | 71/90 |
| 4,311,517 | 1/1982 | Youngman et al. | 71/121 |
| 4,343,647 | 8/1982 | Dunbar et al. | 71/76 |

OTHER PUBLICATIONS

Ford et al., Chem. Abst., vol. 84 (1976) 1241a.

*Primary Examiner*—Catherine L. Mills
*Attorney, Agent, or Firm*—Estelle J. Tsevdos; Alphonse R. Noë

[57] ABSTRACT

Aqueous-soluble compositions of quaternary ammonium plant-growth-regulating compounds possessing improved temperature stability. Compositions contain a mixture of cationic and nonionic surfactants.

10 Claims, No Drawings

AQUEOUS-SOLUBLE COMPOSITIONS FOR ADJUSTING GROWTH OF ORNAMENTAL AND CROP PLANTS

The invention herein described relates to water-soluble compositions of quaternary ammonium compounds. These compounds are plant growth regulators. The compositions of the present invention show improved temperature stability over a wide temperature range. Formulations contain a mixture of cationic and nonionic surfactants.

By way of background, quaternary ammonium compounds having plant growth regulatory properties and uses thereof are disclosed in U.S. Pat. Nos. 3,156,554 and 3,156,555. These patents are incorporated herein by way of reference.

The plant growth regulating properties of 2-(chloroethyl)trimethylammonium chloride were discovered over 20 years ago. Since then, compounds of this type have been used commercially for adjusting the growth of ornamental plants in various areas of the world. In recent years it has been recognized that plant growth regulants of this type help to prevent lodging (falling) of wheat plants, particularly in colder climates. Quaternary ammonium plant growth regulants of this type are normally applied as an aqueous soluble composition which contains a surfactant to enhance wetting of the crop. Although compositions containing a 2-(chloroethyl)trimethylammonium salt have been used successfully throughout the world, such compositions are not wholly satisfactory. When exposed to wide temperature variations over extended periods of time, compositions have been found to exhibit undesirable physical stability (i.e., turbidity, coagulation and separation of layers). This phenomena might be seen, for instance, when containers are stored for long periods of time in cold or hot warehouses.

In light of the foregoing summary of some demands and limitations of formulations used for plant growth regulation which contain a 2-(chloroethyl)trimethylammonium salt as active ingredient, improved compositions are highly desirable. Accordingly, an object of this invention is to provide new and useful water-soluble plant-growth-regulatory compositions containing a 2-(chloroethyl)trimethylammonium salt. This object is manifest in the following description and particularly delineated in the appended claims.

Improved aqueous-soluble compositions containing 30 to 75% by weight of 2-(chloroethyl)trimethylammonium chloride as the active plant-growth-regulatory agent have been unexpectedly found. The improved compositions exhibit superior physical stability over a wider temperature range ($-25°$ to $45°$ C.) when compared to previous compositions. Such concentrated compositions may be diluted for field application. Formulations of the present invention contain a mixture of formula I and/or formula II quaternary ammonium cationic surfactants and formula III and/or formula IV nonionic surfactants.

The formula I and formula II cationic surfactants referenced above which are suitable for use in combinations of the invention are represented by the following structural formulae:

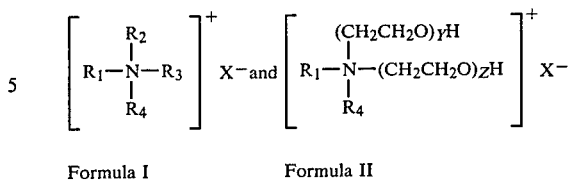

Formula I        Formula II wherein $R_1$, $R_2$ and $R_3$ are selected from $C_1$ to $C_4$ alkyl, $R_4$ is selected from $C_6$ to $C_{18}$ alkyl or alkenyl and X is chlorine, bromine, iodine, or nitrate wherein the sum of Y+Z is defined as a range of 2 to 20; wherein formula I and formula II compounds are used in combination with formula III and formula IV compounds as described below, either individually or a mixture thereof. The following structural formulae represent nonionic surfactants:

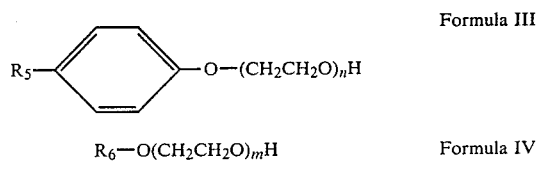

Formula III

Formula IV wherein $R_5$ is selected from $C_7$ to $C_{15}$ alkyl or alkenyl, n is an integer of 6 to 16, $R_6$ is selected from $C_{10}$ to $C_{18}$ alkyl and m is an integer of 6 to 22.

The invention relates in particular to aqueous soluble compositions containing on a weight basis 30 to 75% (preferably about 40 to 55%) of the quaternary ammonium plant growth regulant 2-(chloroethyl)trimethylammonium chloride, 0.08 to 4.8% of a cationic surfactant of formula I, wherein $R_1$, $R_2$ and $R_3$ are methyl, $R_4$ is $C_{12}$ to $C_{14}$ alkyl, X is chlorine or nitrate, and/or a formula II cationic surfactant, wherein $R_1$ is methyl, $R_4$ is $C_{12}$ to $C_{14}$ alkyl, X is chlorine or nitrate and the sum of Y and Z is an integer in the range of 2 to 20; in combination with 0.08 to 4.8% by weight of a nonionic polyether surfactant of formula III, wherein $R_5$ is $C_7$ to $C_{15}$ alkyl, n is an integer ranging from 6 to 16 and/or a formula IV polyether, wherein $R_6$ is $C_{10}$ to $C_{18}$ alkyl and m is an integer ranging from 6 to 22.

Further, the ratio of the cationic surfactant to nonionic surfactant is in the range of 20/80 to 80/20 wherein the total weight percent of said surfactant combination is from 0.4 to 6% by weight of the total combination. Optionally, up to 5% (preferably 0.5 to 3.0%) by weight of a $C_1$-$C_4$ alcohol (i.e., isopropanol or methanol), or benzyl alcohol may be added to the formulation with sufficient water being added to total the composition to 100%.

By the above method a typical aqueous soluble composition may be prepared by admixing 50 g of an aqueous solution containing 63% by weight of 2-(chloroethyl)trimethylammonium chloride with 1.2 g of laurylmethyl-dihydroxyethyl ammonium chloride, 0.8 g of polyoxyethylene-nonylphenylether (wherein n is an integer of 9 to 11) and 3 g of isopropyl alcohol with water in sufficient quantity to total 100 ml of solution.

The preferred combinations of the present invention possess improved physical stability in a temperature range sufficiently broad to allow their use year-around under a variety of climatic conditions.

Surprisingly, the aqueous soluble compositions of the plant-growth-regulating compositions of the invention also demonstrate improved efficacy in reducing the relative stem growth of ornamental and crop plants to which they are applied.

EXAMPLE 1

Preparation of aqueous soluble 2-(chloroethyl)trimethylammonium chloride compositions The appropriate amounts of the quaternary ammonium plant growth regulant, such as 2-(chloroethyl)-trimethylammonium chloride, in aqueous solution at pH 5 to 7 is admixed with the desired amount of the cationic formula I and/or formula II surfactant and the appropriate amount of the nonionic formula III and/or formula IV surfactant. If so desired, alcohol (i.e., $C_1-C_4$ alkyl or benzy alcohol) may be added to the above solution, followed by dilution with water to the desired volume.

Table I presents a description of the various cationic and nonionic surfactants employed in formulations of the present invention. Compositions of 2-(chloroethyl)-triethylammonium chloride, each of which utilizes a selected surfactant or surfactant blend, are presented in Table II. It should be noted that several surfactants are available commercially only as proprietary unspecified mixtures, and/or combinations of the desired cationic and nonionic polyoxyethylene surfactants (c.f., surfactants of Table I where (n) numbers are unavailable and trade names are provided).

TABLE I

| Surfactant | (n) | Type | Chemical Name |
|---|---|---|---|
| A | (12) | Cationic | Polyoxyethylene alkyl aryl ether with cetyl trimethyl ammonium nitrate |
| B | NA* | Cationic | Lauryl trimethyl ammonium chloride |
| C | (12) | Cationic/nonionic | Polyoxyethylene alkyl aryl ether with A as above |
| D | (10) | Cationic/nonionic | Polyoxyethylene alkyl aryl ether with A as above |
| E | (10) | Cationic/nonionic | Polyoxyethylene alkyl aryl ether with lauryl methyl dihydroxy ethyl ammonium chloride |
| F | (8) | Nonionic | Polyoxyethylene nonyl phenyl ether |
| G | (10) | Nonionic | Polyoxyethylene nonyl phenyl ether |
| H | (11) | Nonionic | Polyoxyethylene nonyl phenyl ether |
| I | (10) | Nonionic | Polyoxyethylene nonyl phenyl ether |
| J | (10–31) | Nonionic | Polyoxyethylene octyl phenyl ether |
| K | (20) | Nonionic | Polyoxyethylene oleyl ether |
| L | (9) | Nonionic | Polyoxyethylene oleyl ether |
| M | (8) | Nonionic | Polyoxyethylene oleyl ether |
| N | (8) | Nonionic | Polyoxyethylene lauryl ether |
| O | — | Nonionic | *Polyoxyethylene alkyl amine |
| P | — | Nonionic | **Polyoxyethylene sorbitan monolaurate |
| Q | — | Anionic | ***Triethanol amine polyoxyethylene alkyl ether sulfate |
| R | (8) | Nonionic | Polyoxyethylene lauryl ether |

*NA = Not Applicable
*Anstex-N-100 (available from Toho Chemicals)
**Sorban T-20 (available from Toho Chemicals)
***Emal 20-T (available from Kao-Atlas)

TABLE II

Water-soluble compositions of 2-(chloroethyl)trimethylammonium chloride (CCC)

| Formulation No. | CCC Solution (a.i. 63%) wt % | Surfactant Cationic | Amt. (wt %) | Non-ionic $(CH_2CH_2O)_n$ | Amt. (Wt %) | Solvent | % | D.I. water to make % |
|---|---|---|---|---|---|---|---|---|
| 1 | 73 | — | — | P | 2.0 | — | — | 100 |
| 2 | 73 | — | — | F | 2.0 | — | — | 100 |
| 3 | 73 | — | — | G | 2.0 | — | — | 100 |
| 4 | 73 | — | — | N | 2.0 | — | — | 100 |
| 5 | 73 | C | 4.0 | C | — | — | — | 100 |
| 6 | 73 | D | 4.0 | D | — | — | — | 100 |
| 7 | 73 | C | 2.0 | C | — | — | — | 100 |
| 8 | 73 | D | 2.0 | D | — | — | — | 100 |
| 9 | 73 | A | 2.0 | N | 2.0 | — | — | 100 |
| 10 | 73 | A | 2.0 | I | 2.0 | — | — | 100 |
| 11 | 73 | A | 2.4 | I | 1.6 | — | — | 100 |
| 12 | 73 | — | — | I | 2.0 | — | — | 100 |
| 13 | 73 | O | 2.0 | I | 2.0 | — | — | 100 |
| 14 | 73 | A | 1.2 | I | 0.8 | — | — | 100 |
| 15 | 73 | — | — | H | 2.0 | — | — | 100 |
| 16 | 73 | A | 2 | — | — | — | — | 100 |
| 17 | 73 | — | — | I | 2.0 | — | — | 100 |
| 18 | 73 | A | 1.2 | I | 0.8 | Ethylene glycol | 2.0 | 100 |
| 19 | 73 | A | 1.2 | I | 0.8 | Methyl alcohol | 2.0 | 100 |
| 20 | 73 | A | 1.2 | I | 0.8 | Isopropyl alcohol | 2.0 | 100 |
| 21 | 73 | — | — | Q* L | 3.5 4.5 | Methyl alcohol | 2.0 | 100 |
| 22 | 73 | — | — | Q L | 4.0 4.0 | Methyl alcohol | 2.0 | 100 |
| 23 | 73 | B | 5.0 | J (n = 10) | 2.0 | — | — | 100 |
| 24 | 73 | B | 2.0 | J (n = 10) | 0.8 | Isopropyl alcohol | 3.0 | 100 |
| 25 | 73 | B | 2.5 | M | 1.0 | — | — | 100 |
| 26 | 73 | B | 2.5 | L | 1.0 | — | — | 100 |

TABLE II-continued

Water-soluble compositions of 2-(chloroethyl)trimethylammonium chloride (CCC)

| Formulation No. | CCC Solution (a.i. 63%) wt % | Surfactant Cationic | Amt. (wt %) | Non-ionic $(CH_2CH_2O)_n$ | Amt. (Wt %) | Solvent | % | D.I. water to make % |
|---|---|---|---|---|---|---|---|---|
| 27 | 73 | B | 1.25 | R | 0.5 | — | — | 100 |
| 28 | 73 | B | 1.25 | J (n = 11) | 0.5 | — | — | 100 |
| 29 | 73 | B | 2.0 | J (n = 20) | 0.8 | Isopropyl alcohol | 3.0 | 100 |
| 30 | 73 | B | 2.0 | J (n − 31) | 0.8 | Isopropyl alcohol | 3.0 | 100 |
| 31 | 73 | A | 1.2 | I | 0.8 | — | — | 100 |
| 32 | 73 | A | 1.2 | I | 0.8 | Isopropyl alcohol | 0.5 | 100 |
| 33 | 73 | A | 1.2 | I | 0.8 | Isopropyl alcohol | 1.0 | 100 |
| 34 | 73 | A | 1.2 | I | 0.8 | Isopropyl alcohol | 2.0 | 100 |
| 35 | 73 | A | 1.2 | I | 0.8 | Isopropyl alcohol | 4.0 | 100 |
| 36 | 73 | — | — | P | 2.0 | Benzyl alcohol | 0.5 | 100 |
| 37 | 73 | A | 1.2 | G | 0.2 | Isopropyl alcohol | 2.0 | 100 |
|  |  |  |  | I | 0.6 |  |  |  |
| 38 | 73 | A | 1.2 | G | 0.2 | — | — | 100 |
|  |  |  |  | I | 0.6 |  |  |  |
| 39 | 73 | A | 1.0 | I | 1.0 | Isopropyl alcohol | 2.0 | 100 |
| 40 | 73 | A | 0.8 | I | 1.2 | Isopropyl alcohol | 2.0 | 100 |
| 41 | 73 | A | 1.1 | I | 0.9 | Isopropyl alcohol | 4.0 | 100 |
| 42 | 73 | A | 1.1 | I | 0.9 | Isopropyl alcohol | 2.0 | 100 |
| 43 | 73 | B | 1.2 | I | 0.8 | — | — | 100 |
| 44 | 73 | B | 2.0 | I | 0.8 | — | — | 100 |
| 45 | 73 | B | 2.5 | K | 1.0 | — | — | 100 |
| 46 | 73 | B | 1.2 | K | 0.5 | — | — | 100 |
| 47 | 73 | A | 1.2 | I | 0.8 | Isopropyl alcohol | 2.0 | 100 |
| 49 | 73 | B | 2.0 | J (n = 11) | 0.8 | Isopropyl alcohol | 3.0 | 100 |
| 50 | 73 | A | 1.2 | I | 0.8 | Isopropyl alcohol | 10.0 | 100 |
| 51 | 73 | A | 0.8 | I | 1.2 | Isopropyl alcohol | 10.0 | 100 |
| 52 | 73 | B | 2.5 | K | 1.0 | Isopropyl alcohol | 3.0 | 100 |
| 53 | 73 | B | 2.0 | P | 1.8 | Benzyl alcohol | 0.5 | 100 |
| 54 | 73 | B | 2.0 | G | 1.0 | Benzyl alcohol | 3.0 | 100 |
| 55 | 73 | E | 2.0 | E | — | — | — | 100 |
| 56 | 73 | E | 2.0 | E | — | Isopropyl alcohol | 3.0 | 100 |
| 57 | 73 | E | 4.0 | E | — | Isopropyl alcohol | 3.0 | 100 |
| 58 | 73 | B | 2.0 | J (n = 11) | 0.8 | — | — | 100 |
| Control Combination | 73 | Surfactant* | 1.8 | — | — | Benzyl alcohol | 0.5 | 100 | a.i. = active ingredient
D.I. = deionized
*an anionic surfactant

EXAMPLE 2

Several of the more preferred combinations described in Example I were prepared and their physical stability evaluated as to cloudiness, oil separation, pH, crystallization, color, mold formation and assay of active ingredient at various temperatures and time intervals as described below. The results of this evaluation are summarized in Table III.

Cloudiness was assessed by macroscopic observation. Solutions were evaluated using a scale where (+) indicates cloudy and (−) indicates a clear solution.

Oil separation was determined by macroscopic observation using a scale where (+) indicates separation and (−) indicates a stable solution.

The pH of test solutions was determined using a Hitachi-Horiba pH meter (type H-7).

Assays (% w/w) of solutions were made using a titration method involving a silver nitrate solution. The 2-(chloroethyl)trimethylammonium chloride content is calculated from organic chlorine by separately determining a total of organic and inorganic chloride and inorganic chlorine.

Crystallization, color, and mold determinations were made by macroscopic observation.

TABLE III

Results of stability test

| Formulation | | 49 | 55 | 56 | 57 | Control combination |
|---|---|---|---|---|---|---|
| pH | Initial | 6.08 | 6.32 | 6.28 | 6.19 | 6.01 |
|  | 45° C./1M | 2.32 | 1.97 | 2.00 | — | 2.15 |
|  | R.T./1M | 4.79 | 4.86 | 4.86 | — | 4.33 |
|  | −5° C./1M | 6.16 | 6.47 | 6.49 | — | 5.98 |
|  | −25° C./1M | 5.59 | 5.00 | 5.22 | — | 5.06 |
| Assay % w/w | Initial | 47.3 | 48.4 | 46.8 | — | 46.2 |
|  | 45° C./1M | 47.8 | 47.5 | 48.1 | — | 46.3 |
|  | 45° C./3M | 46.6 | 48.0 | 48.2 | — | 45.6 |
| Oil separation | 45° C./3M | — | — | — | — | + |
|  | R.T./3M | — | — | — | — | + |
|  | −5° C./3M | — | — | — | — | — |
|  | −25° C./3M | — | — | — | — | — |
| Cloudiness | 45° C./3M | — | — | — | — | — |
|  | R.T./3M | — | — | — | — | + |
|  | −5° C./3M | — | — | — | — | — |
|  | −25° C./3M | + | — | — | — | — |
| Crystallization | R.T./3M | — | — | — | — | — |
|  | −5° C./3M | — | — | — | — | — |
|  | −25° C./3M | — | — | — | — | — |
| Color | 45° C./3M | N | N | N | N | N |
|  | R.T./3M | N | N | N | N | N |
| Mold | R.T./3M | — | — | — | — | — |
|  | 45° C./3M | — | — | — | — | — |

M = month of storage time
Expression:
Oil separation +: Marginal
Cloudiness −: Negative
Crystallization +: Found
Color N: No change
Mold −: No growth From the data reported in Table III, it can be seen that the physical stability (e.g., oil separation; cloudiness) of the preferred compositions of the invention is superior to the control formulation over a wide temperature range for extended periods of time.

EXAMPLE III

Biological Activity

Wheat Haruhikari

Ten seeds were sown at a depth of 2 cm in each 133 cm² pot containing a clay loam soil prepared by mixing sand, clay and humus at the rate of 1:2:1. After thinning to seven healthy plants at a plant height of 31.1 cm and five leaves, uniform treatment from a spray gun was made at a rate of 10 ml/1000 cm² (corresponding to 1000 liter/ha at three dosage rates of 0.5, 1.0 and 1.5 kg/ha). Plant heights were recorded with five plants from each pot on the 40th day after treatment (DAT).

This treatment was replicated six times for each of the compositions tested. Temperature variations during testing ranged from 26.6° to 29.9° C. during the day to 8.4° to 10.5° C. at night.

The effects of treatment on the plant height of wheat of an untreated control, the preferred No. 56 and No. 49 compositions, standard compositions No. 1 and No. 2, and the unformulated technical plant growth regulant (46% a.i.) are presented in Table IV below.

TABLE IV

Effects of four formulations of 2-(chloroethyl)trimethylammonium chloride (CCC) on the height of Wheat

| | Average plant height (cm)/pot | | | | | |
|---|---|---|---|---|---|---|
| Rate kg a.i./ha | Control | No. 56 | No. 49 | Standard No. 1 | Standard No. 2 | Tech. (ccc) 46% a.i. |
| 0.5 | 57.7 | 53.1 | 55.5 | 57.7 | 54.9 | 56.9 |
| (%)* | (100.0) | (92.0) | (96.2) | (100.0) | (95.1) | (98.6) |
| 1.0 | 57.7 | 52.2 | 52.9 | 54.5 | 56.2 | 54.6 |
| (%) | (100.0) | (90.5) | (91.7) | (94.5) | (97.4) | (94.6) |
| 1.5 | 57.7 | 50.0 | 50.7 | 51.3 | 51.5 | 53.0 |
| (%) | (100.0) | (86.7) | (87.9) | (88.9) | (89.2) | (91.9) |

*Plant height as a percentage of untreated check
a.i. = active ingredient

It can be seen from the above table that the No. 56 formulation significantly (P<0.01) reduced the plant height by 8%, 9.5% and 13.3% in comparison with the control at concentrations of 0.5, 1.0 and 1.5 kg a.i./ha. The No. 49 formulation at concentrations of 1.0 and 1.5 kg a.i./ha significantly (P<0.01) reduced the plant height by 8.3% and 12.9%.

There was no significant effect of the treatment on the tillering of the plants and no phytotoxic effects were observed during the course of the experiment.

What is claimed is:

1. A stable, aqueous soluble composition for adjusting growth of ornamental and crop plants, said aqueous soluble composition exhibiting temperature stability at temperatures of $-25°$ C. to 45° C., comprising: about 30% to 75% by weight, of 2-(chloroethyl)trimethylammonium salt, as the active ingredient; a cationic surfactant or mixture of cationic surfactants, having the structural formulae, I and II,

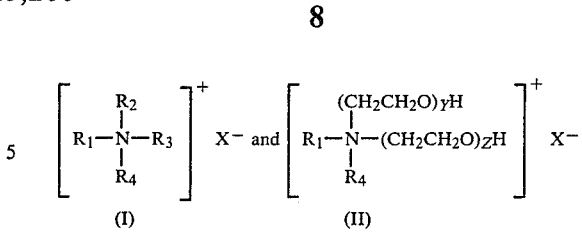

wherein $R_1$, $R_2$ and $R_3$ are each $C_1$-$C_4$ alkyl; $R_4$ is $C_{10}$-$C_{18}$ alkyl or alkenyl, and Y is chlorine, bromine, iodine or nitrate; where the sum of (Y+Z) is defined as a range of 2 to 20; a nonionic surfactant or mixture of nonionic surfactants depicted by structural formulae III and IV,

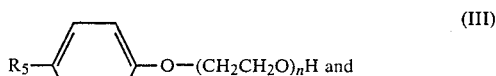

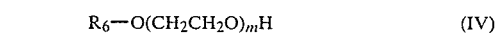

wherein $R_5$ is $C_7$-$C_{15}$ alkyl or alkenyl; n is an integer of 6–16; $R_6$ is $C_{10}$-$C_{18}$ alkyl or alkenyl; m is an integer of 6–22, wherein the ratio of said cationic to said nonionic surfactants or mixtures thereof is 20/80 to 80/20, and the total cationic and nonionic surfactant combination is about 0.4% to 6.0% of said total composition; a $C_1$-$C_4$ alcohol or benzyl alcohol; and sufficient water to total said composition to 100%.

2. A stable, aqueous soluble composition according to claim 1, said composition comprising, on a weight basis: 40%–55% 2-(chloroethyl)trimethylammonium chloride, as active ingredient; 0.08% to 4.8% of said cationic surfactant; 0.08%–4.8% of said nonionic surfactant, with said surfactant combination comprising 0.4% to 6% of said composition; and 0.0% to 5%, of said $C_1$-$C_4$ alcohol or benzyl alcohol; and sufficient water to total said composition to 100%.

3. An aqueous soluble composition according to claim 2 wherein the cationic surfactant is lauryl trimethylammonium chloride or lauryl methyl dihydroxyethyl ammonium chloride.

4. An aqueous soluble composition according to claim 2 wherein the nonionic surfactant is chosen from the formula III compound, wherein $R_5$ is nonyl, octyl or oleyl, and n is an integer of from 8 to 20.

5. An aqueous soluble compositions according to claim 2 wherein 0 to 5% by weight of the final combination may be an alcohol chosen from methanol, isopropanol ethanol, butanol or benzyl alcohol.

6. A composition according to claim 2 wherein the cationic surfactant is lauryl trimethylammonium chloride and the nonionic surfactant is a polyoxyethylene octyl phenyl ether wherein n is 11 and 0.5 to 3% by weight of isopropyl alcohol and the cationic surfactant to nonionic surfactant ratio is 2.5/1 and the total weight percent of surfactants is from 2 to 4%.

7. A composition according to claim 2 wherein the cationic surfactant is lauryl methyl dihydroxyethyl ammonium chloride and the nonionic surfactant is a polyoxyethylene nonyl phenyl ether, wherein n is 10, and 0.5 to 3% by weight of isopropyl alcohol, and the cationic surfactant to nonionic surfactant ratio is 0.66/1, and the total weight percent of the surfactants is from 2 to 4%.

8. A method for controlling the relative stem growth of ornamental and crop plants, said method comprising:

applying thereto a stable-aqueous-soluble-plant growth regulating amount of a composition, said composition exhibiting temperature stability at temperatures of −25° C. to 45° C. and said composition containing, on a weight basis, 30% to 75% 2-(chloroethyl)trimethylammonium chloride; 0.08% to 4.8% of a cationic surfactant or mixture of cationic surfactants having the structural formulae I and II,

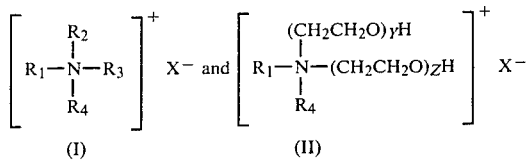

wherein $R_1$, $R_2$ and $R_3$ are each $C_1$-$C_4$ alkyl; $R_4$ is $C_{10}$-$C_{18}$ alkyl or alkenyl; and X is chlorine, bromine, iodine or nitrate, where the sum of (Y+Z) is defined as 2 to 20; 0.08% to 4.8%, by weight, of a nonionic surfactant or mixture of nonionic surfactants having the structural formulae III and IV,

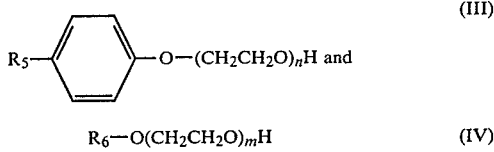

wherein $R_5$ is $C_7$-$C_{15}$ alkyl or alkenyl; n is an integer of 6-16; $R_6$ is $C_{10}$-$C_{18}$ alkyl or alkenyl; and m is an integer of 6-22; wherein the ratio of cationic to nonionic surfactants or mixture thereof is 20/80 to 80/20; said surfactant combination is 0.4% to 6%, by weight, of said composition; 0.0% to 5%, by weight, of said $C_1$-$C_4$ alcohol or benzyl alcohol; and sufficient water to total said composition to 100%.

9. A method for reducing the height of ornamental and crop plants by applying thereto a plant growth regulating amount of a composition according to claim 6.

10. A method for reducing the height of ornamental and crop plants by applying thereto a plant growth regulating amount of a composition according to claim 7.

* * * * *